United States Patent [19]

Reed

[11] Patent Number: 5,344,827
[45] Date of Patent: * Sep. 6, 1994

[54] STEROID SULPHATAS INHIBITORS

[75] Inventor: Michael J. Reed, London, United Kingdom

[73] Assignee: Imperial College of Science, Technology and Medicine, London, United Kingdom

[*] Notice: The portion of the term of this patent subsequent to Jan. 25, 2011 has been disclaimed.

[21] Appl. No.: 143,071

[22] Filed: Oct. 26, 1993

Related U.S. Application Data

[63] Continuation of Ser. No. 779,067, Oct. 18, 1991, Pat. No. 5,281,587.

[30] Foreign Application Priority Data

Feb. 21, 1990 [GB] United Kingdom ............... 9003939

[51] Int. Cl.$^5$ .................. C07J 51/00; A61K 31/56
[52] U.S. Cl. .................................. 514/169; 514/170
[58] Field of Search ........................... 514/169, 170

[56] References Cited

U.S. PATENT DOCUMENTS

| 2,878,157 | 3/1959 | Bloom et al. | 514/169 |
| 4,150,126 | 4/1979 | Fex et al. | 514/169 |
| 5,281,587 | 1/1994 | Reed | 514/169 |

FOREIGN PATENT DOCUMENTS

| 0016594 | 10/1980 | European Pat. Off. . |
| 0644486 | 1/1979 | U.S.S.R. . |

OTHER PUBLICATIONS

Steroids, vol. 33, No. 5, May 1979, R. I. Cox et al, p. 549.

*Primary Examiner*—Nathan M. Nutter
*Attorney, Agent, or Firm*—Hedman, Gibson & Costigan

[57] ABSTRACT

Novel steroid 3-thiophosphonates are disclosed which are useful as steroid sulphatase inhibitors.

6 Claims, 3 Drawing Sheets

KEY ENZYMES IN STEROIDOGENESIS:-
1. SULPHATASE   2. AROMATASE   3. DEHYDROGENASE   4. 5α REDUCTASE

STEROID SULPHATAS INHIBITORS

This is a continuation of application Ser. No. 07/779,067, filed Oct. 18, 1991 and now U.S. Pat. No. 5,281,587.

FIELD OF INVENTION

This invention relates to steroid sulphatase inhibitors, and pharmaceutical compositions containing them.

Steroid precursors, or pro-hormones, having a sulphate group in the 3-position of the steroid nucleus, referred to hereinafter simply as steroid sulphates, are known to play an important part as intermediates in steroid metabolism in the human body. Oestrone sulphate and dehydroepiandrosterone (DHA) sulphate, for example, are known to play an important role as intermediates in the production, in the body, of oestrogens such as oestrone and oestrodiol, see the steroid metabolism chart presented in the accompanying drawing. Oestrone sulphate, in particular, is known, for example, to represent one of the major circulating oestrogen precursors particularly in post-menopausal women.

Not only that, but oestrogens such as oestrone and oestradiol, particularly the over-production thereof, are strongly implicated in malignant conditions, such as breast cancer, and the control of oestrogen production is the specific target of many anti-cancer therapies, both chemotherapy and surgical, e.g. oopherectomy and adrenalectomy. So far as chemotherapy is concerned, efforts have so far tended to concentrate on aromatase inhibitors, i.e. compounds which inhibit aromatase activity, which activity is involved, as the accompanying oestrogen metabolic flow diagram shows, in the conversion of androgens such as androstenedione and testosterone to oestrone and oestradiol respectively.

OBJECTS OF THE INVENTION

The present invention, on the other hand, targets a different point in the oestrogen metabolic pathway, or rather two different points, that is to say the conversion of DHA sulphate and oestrone sulphate to DHA and oestrone, respectively, by steroid sulphatase activity. Whether the same enzyme is responsible for both reactions, or whether two separate sulphatase enzymes are involved is presently unknown, but that is immaterial so far as the present invention is concerned, since the aim is to inhibit steroid sulphatase activity in general, and not to target a particular steroid sulphatase.

SUMMARY OF INVENTION

The present invention is based on the discovery that steroid sulphatase activity is strongly inhibited by replacing the sulphate group in the 3-position with a monoalkyl, preferably lower ($C_1$–$C_6$) alkyl thiophosphonate group, i.e. a group of the formula

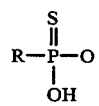

where R is alkyl.

DETAILED DESCRIPTION

Figure 1:
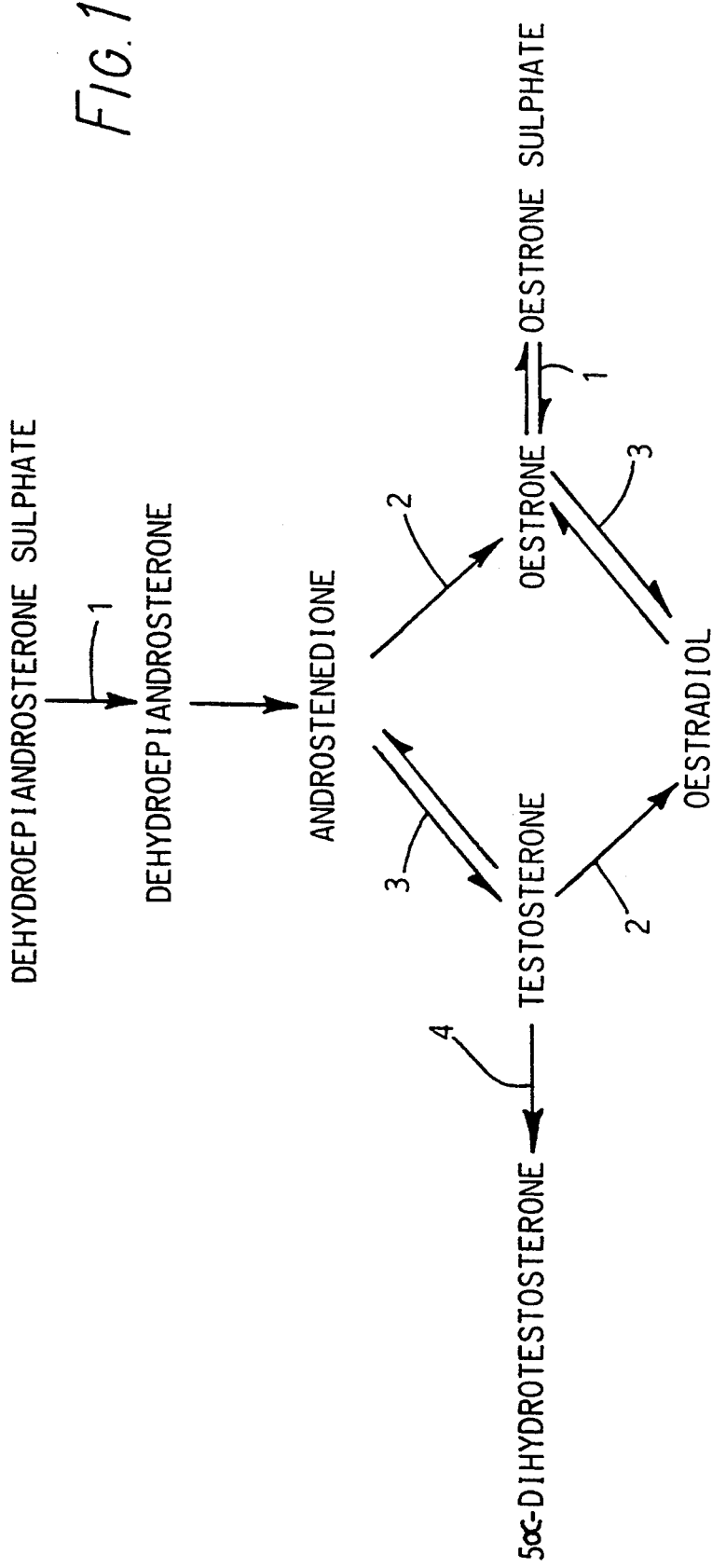
FIG. 1 is the oestrone metabolism chart showing the metabolic pathways and enzymes involved in the production of oestradiol in vivo.

In accordance with the present invention, therefore, there are provided pharmaceutical preparations for the treatment of oestrogen dependent turnouts containing as asteroid sulphatase inhibitor therein an effective amount of a compound of the formula:

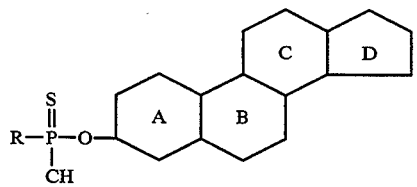

where R is alkyl, preferably $C_1$–$C_6$ alkyl, and the ring system A B C D is a steroid nucleus selected from the group consisting of oestrone, dehydroepiandrosterone, substituted oestrones and substituted dehydroepiandrosterones, or a pharmaceutically acceptable salt thereof.

In a specific embodiment, there are provided anti-oestrogen pharmaceutical preparations having steroid sulphatase inhibitory activity and containing as the steroid sulphatase inhibitor either or both of oestrone-3-(mono)alkyl thiophosphonate, viz: compounds of the formulae

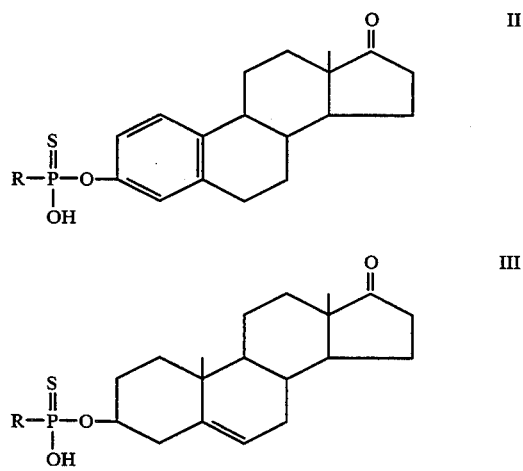

respectively, where R is as defined above, preferably methyl, or a pharmaceutically acceptable salt thereof.

In in vitro studies it has been shown that such 3-monoalkylthiophosphonate steroid derivatives strongly inhibit steroid sulphatase activity, i.e. the corresponding steroid sulphate, although such theoretical explanation in no way limits or categorises the present invention.

The thiophosphonate steroid derivates used in accordance with this invention can be obtained by reaction of the corresponding sterol with an alkyl thiophosphonic acid chloride or dichloride, i.e. the reaction:

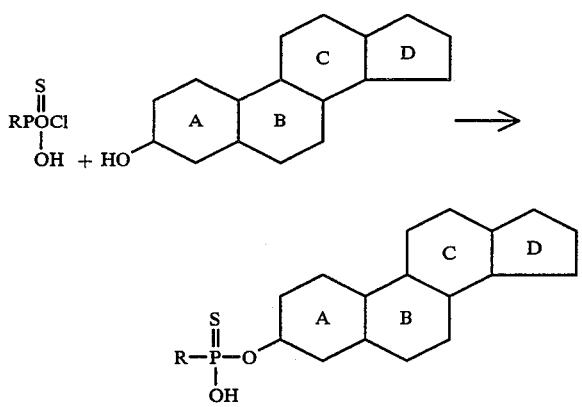

possibly with one or more preliminary steps to introduce suitable protecting groups to protect other functional groups in the sterol, and which protective groups are removed at the end of the reaction. Within the above formula the steroid ring system ABCD may contain non-interfering susbstituents. In particular, either R or the ring system ABCD may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

In the above formulae, the steroid ring system ABCD is preferably oestrone or dehydroepiandrosterone. Other suitable steroid ring systems are:

substituted oestrones, viz:
2-OH-oestrone
2-methoxy-oestrone
4-OH-oestrone
6α-OH-oestrone
7α-OH-oestrone
16α-OH-oestrone
16β-OH-oestrone oestradiols and substituted oestradiols, viz:
2-OH-17β-oestradiol
2-Methoxy-17β-oestradiol
4-OH-17β-oestradiol
6α-OH-17β-oestradiol
7α-OH-17β-oestradiol
16α-OH-17α-oestradiol
16β-OH-17α-oestradiol
16β-OH-17β-oestradiol
17α-oestradiol
17β-oestradiol
17α-Ethinyl-17β-oestradiol oestriols and substituted oestriols, viz:
oestriol
2-OH-oestriol
2-Methoxy-oestriol
4-OH-oestriol
6α-OH-oestriol
7α-OH-oestriol Substituted dehydroepiandrosterones, viz:
6α-OH-dehydroepiandrosterone
7α-OH-dehydroepiandrosterone
16α-OH-dehydroepiandrosterone
16β-OH-dehydroepiandrosterone For pharmaceutical administration, the steroid sulphatase inhibitors of this invention can be formulated in any suitable manner utilising conventional pharmaceutical formulating techniques and pharmaceutical carriers, exipients, diluents etc. and usually for parenteral administration. Approximate effective dose rates are in the range 100 to 800 mg/day depending on the individual activities of the compounds in question and for a patient of average (70kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg. of compound per unit dose. Alternatively and preferably the compounds will be formulated for parenteral administration in a suitable parenterally administrable carrier and providing single daily dosage rates in the range 200 to 800 mg, preferably 200 to 500 more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromarase inhibitor, such as for example, 4-hydroxyandrostenedione (4-OHR). One such combination therapy has already been envisaged herein, i.e. the combination of both oestrone-3-methylthiophosphonate and dehydroepiandrosterone-3-methylthiophosphonate to block both metabolic pathways to oestrone and oestradiol, whether direct from oestrone sulphate or from DHA sulphate via androstenedione and testosterone.

The invention is further illustrated in the following Examples and by the accompanying drawings.

EXAMPLE 1

Preparation of oestrone-3-methylthiophosphanate

To a solution of methylthiophosphonic acid dichloride (3.6 g) in dry collidine (16 ml), cooled in ice, was added a solution of oestrone (2.2 g) in dry collidine (12 ml), dropwise over 2 hours with stirring. The reactants were allowed to warm to ambient temperature, stirred a further 24 hours and poured over ice. The aqueous phase was extracted with ethyl acetate and the solvent removed from the extracts by evaporation. Repeated codistillation with water on a rotary evaporator removed excess collidine. The residual gum was dissolved in phosphate buffer (0.25 M, pH 8, 20 ml) by gently warming and the cloudy solution extracted with ethyl acetate.

After adjusting the aqueous phase to pH 2, an oil separated which solidified after cooling and trituration. Oestrone-3-methylthiophosphonate (1.4 g) was obtained as a hemihydrate after crystallisation from methanol-water. It had mp 95°–98° C. after which it partly recrystallised and melted again at 157°–160° C. $^1$Hnmr (CDCl$_3$): ppm 1.96 (P-methyl, d, J=16 Herz); 0.86 ($C_{18}$ methyl, s). M+ at m/e=364. (Gas chromatography mass spectrometry).

EXAMPLE 2

Preparation of DHA-3-(methylthiophosphonate)

Figure 3:
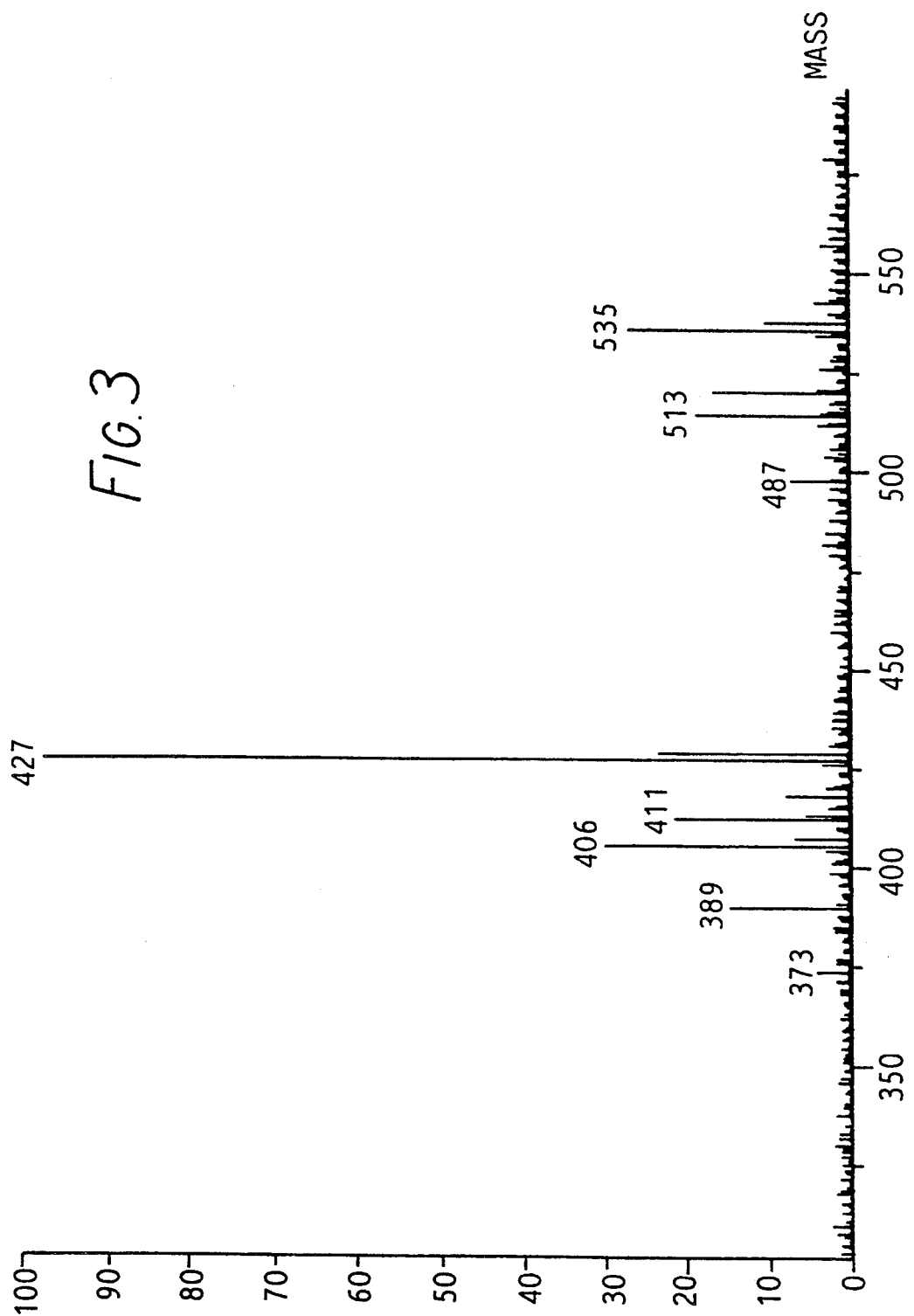
FIG. 3 is the GC-MS spectrum of DHA-3-methylthiophosphonate ester.

The procedure of Example 1 was repeated save that oestrone was replaced by the same quantity of dehydroepiandrosterone. The product DHA-3-(methylthiophosphonate) ester was analysed by gas chromatography mass spectrometry to give GC-MS spectrum as shown in FIG. 3.

EXAMPLE 3

Inhibition of Sulphatase Activity in MDA Cells

Sulphatase activity is defined as: Arylsulphatase; phenol sulphatase EC 3.2.6.1. One unit will hydrolyse 1.0 μmole of p-nitrocatechol sulphate per hour at pH 5.0 at 37° C.

Oestrone sulphatase activity was measured in vitro using intact MDA-MB-231 breast cancer cells in the presence of a range of putative inhibitors of the enzyme, the results of which are shown in Tables I and II. Triplicate 25 cm² monolayer cultures of MDA-MB-231 cells and triplicate flasks without cells (blanks) were incubated with medium containing and as substrate $^3$H oestrone sulphate (2nM, N.E.N., Dupont) with or without oestrone-3-methylthiophosphonate (10μM) for 3 hours at 37° C. At the end of the 3 hour incubation period a recovery marker was added (5000 cpm of $^{14}$C oestrone from Amersham International plc). Medium (1 ml) was then removed from each sample and non-polar products formed (i.e. oestrone and oestradiol) were extracted with toluene (5 ml).

The amount of product formed was quantified by counting 1 ml of the toluene extract in a liquid scintillation spectrometer.

The cell line, MDA-MB-231, is a breast cancer cell line that is widely used to study the control of breast cancer cell growth. It is a receptor negative (ER-, PR-, AR-) cell line and is widely available in the USA from the American Type Culture Collection (ATCC) and in the UK (e.g. from Glaxo plc or from the Imperial Cancer Research Fund).

TABLE 1

Oestrogen Sulphatase Activity in MDA-MB-231 cells in the presence of Oestrone-3-Methylthiophosphonate

| Inhibitor | Oestrogen Sulphatase Activity (fmoloestrogens/3 hr/10⁶cells) | % of control |
|---|---|---|
| None (control) | 124.3 ± 2.1$^M$ | — |
| Oestrone-3-methyl-thiophosphonate | 10.2 ± 0.7*** | 8.2 |

$^M$Mean ± S.D., n = 3
*p 0.05
**p 0.01
***p 0.001

An identical experimental protocol was used to generate the results in Table II except that oestrone-3-methylthiophosphonate was replaced by the inhibitors listed under column 1 at a concentration of 10 μM.

Figure 2:
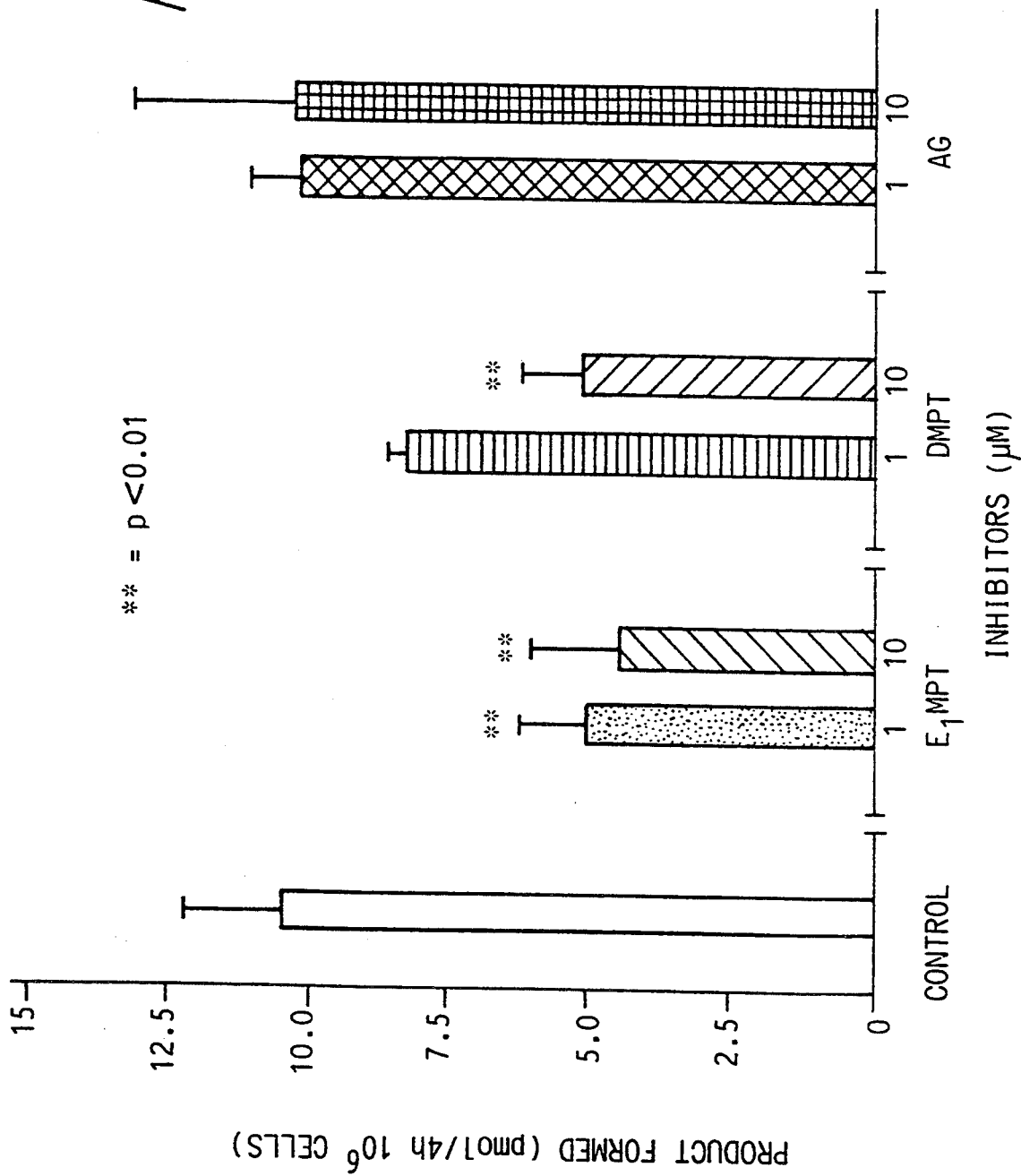
FIG. 2 is a bar chart showing the inhibiting effect of oestrone- and DHA-3-(methylthiophopshonate) on sulphatase activity in MDA-MB-231 cells.

The results of a third experiment, in which DHA sulphate was used as substrate and both oestrone-3-methylthiophosphonate (EIMPT) and DHAS-3-methylthiophosphonate (DMPT), are shown in FIG. 2 of the accompanying drawings. Both oestrone-3-methylthiophosphonate and dehydroepiandrosterone-3-methylthiophosphonate (10 μM) inhibited sulphatase activity to a similar degree, that is by approximately 50%.

TABLE II

Oestrogen Sulphatase Activity in MDA-MB-231 cells for other compounds of interest

| Inhibitor (10 μM) | Oestrogen Sulphatase Activity (fmol oestrogens/3 hr/10⁶ cells) | % of control |
|---|---|---|
| None (control) | 105 ± 7$^M$ | — |
| Medroxyprogesterone acetate | 136 ± 8** | 130 |
| Dehydroepiandrosterone sulphate | 73 ± 8** | 70 |
| Danazol | 58 ± 8** | 55 |
| Tamoxifen | 120 ± 5** | 114 |
| 4-Hydroxyandrostenedione | 89 ± 7 | 84 |
| Ethinyloestradiol | 47 ± 5*** | 45 |

$^M$Mean ± S.D., n = 3
*p 0.05
**p 0.01
***p 0.001

Referring in more detail to FIG. 2, this illustrates the inhibiting effect of oestrone-3-methylthiophosphonate (EIMPT) and DHA-3-methylthiophosphonate (DMPT) on steroid sulphatase activity in MDA MB-231 cells using DHA sulphate as substrate. Experimental substrates of the assay system are described in Example 3 above, except that: the medium contained $^3$H DHA sulphate (1 μM, N.E.N., Dupont); the incubation period was for four hours at 37° C.; the recovery marker added after incubation was $^{14}$C DHA (5,000 cpm from Amersham International plc); and the amount of product (DIIA) formed was calculated in terms of pmol/4 hours/10⁶ cells after extraction with toluene. AG=Aminoglutethimide.

I claim:

1. A pharmaceutical preparation comprising in admixture a steroid sulphatase inhibitor and a parenterally administrable carrier wherein the steroid sulphatase inhibitor comprises an effective amount of a steroid-3-thiophosphonate of the formula

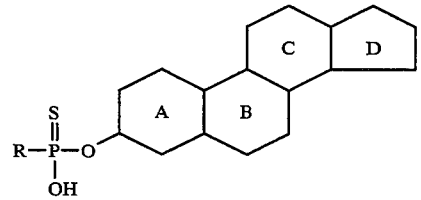

where R=alkyl, and the ring system ABCD represents a substituted or unsubstituted saturated or unsaturated steroid nucleus, or a pharmaceutically acceptable salt thereof.

2. A pharmaceutical preparation according to claim 1, wherein R in the formula of the steroid sulphatase inhibitor is $C_1$–$C_6$ alkyl.

3. A pharmaceutical preparation according to claim 1, wherein R in the formula of the steroid sulphatase inhibitor is methyl.

4. A pharmaceutical preparation comprising, in unit dosage form, a steroid sulphatase inhibitor in admixture with an orally administrable carrier, wherein the said steroid sulphatase inhibitor is a steroid-3-thiophosphonate of the formula

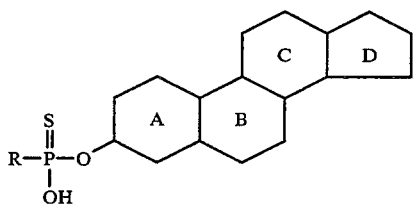

wherein R is alkyl, and the ring system ABCD represents a substituted or unsubstituted, saturated or unsaturated steroid nucleus, or a pharmaceutically acceptable salt thereof, said preparation containing from 100 to 500 mg of said steroid-3-thiophosphonate or salt per unit dose.

5. A preparation according to claim 4, wherein R in the said formula is $C_1$–$C_6$ alkyl.

6. A preparation according to claim 5, wherein R is the said formula is methyl.

* * * * *